(12) United States Patent
Takagi

(10) Patent No.: US 11,504,084 B2
(45) Date of Patent: Nov. 22, 2022

(54) RADIOGRAPHING CONTROL APPARATUS, RADIOGRAPHIC IMAGING APPARATUS AND RADIOGRAPHIC IMAGING SYSTEM

(71) Applicant: Konica Minolta, Inc., Tokyo (JP)

(72) Inventor: Tatsuya Takagi, Mitaka (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 17/306,215

(22) Filed: May 3, 2021

(65) Prior Publication Data

US 2021/0267567 A1 Sep. 2, 2021

Related U.S. Application Data

(63) Continuation of application No. 16/250,308, filed on Jan. 17, 2019, now Pat. No. 11,026,651.

(30) Foreign Application Priority Data

Jan. 19, 2018 (JP) .............................. JP2018-006819
Oct. 16, 2018 (JP) .............................. JP2018-194764

(51) Int. Cl.
*A61B 6/00* (2006.01)
*G06T 7/00* (2017.01)

(52) U.S. Cl.
CPC .............. *A61B 6/544* (2013.01); *A61B 6/488* (2013.01); *A61B 6/5211* (2013.01); *A61B 6/542* (2013.01);
(Continued)

(58) Field of Classification Search
CPC ....... A61B 6/544; A61B 6/488; A61B 6/5211; A61B 6/542; A61B 6/545; G06T 7/0014; G06T 2207/10128
See application file for complete search history.

(56) References Cited

U.S. PATENT DOCUMENTS 5,608,775 A 3/1997 Hassler et al.
8,971,494 B2 3/2015 Tajima
(Continued)

FOREIGN PATENT DOCUMENTS

JP S59174081 A 10/1984
JP H07275230 A 10/1995
(Continued)

OTHER PUBLICATIONS

Non-Final Office Action for corresponding U.S. Appl. No. 16/250,308; dated Sep. 18, 2020.
(Continued)

*Primary Examiner* — David P Porta
*Assistant Examiner* — Gisselle M Gutierrez
(74) *Attorney, Agent, or Firm* — Cantor Colburn LLP

(57) ABSTRACT

A radiographing control apparatus includes a hardware processor. A radiographic imaging apparatus is exposed to a radiation from an irradiating apparatus through the subject. The hardware processor retrieves pre-exposure image data which the radiographic imaging apparatus generates by performing a pre-exposure to the subject at a pre-exposure dose of less than a dose of a subsequent main exposure, and calculates a total dose required to obtain diagnostic image data to be used for diagnosis. The hardware processor outputs a main exposure dose based on the calculated total dose to the irradiating apparatus and the radiographic imaging apparatus. The hardware processor retrieves main exposure image data which the radiographic imaging apparatus generates by performing the main exposure to the subject at the main exposure dose, and combines the main exposure image data with the pre-exposure image data to generate the diagnostic image data.

9 Claims, 10 Drawing Sheets

(52) U.S. Cl.
CPC ............ *G06T 7/0014* (2013.01); *A61B 6/545* (2013.01); *G06T 2207/10128* (2013.01)

(56) References Cited

U.S. PATENT DOCUMENTS

| | | |
|---|---|---|
| 10,188,366 B2 | 1/2019 | Beak |
| 10,194,883 B2 | 2/2019 | Morita |
| 10,470,727 B2 | 11/2019 | Ota et al. |
| 2006/0237648 A1 | 10/2006 | Bushberg |
| 2010/0006764 A1 | 1/2010 | Bushberg |
| 2013/0148782 A1* | 6/2013 | Tajima .................. A61B 6/548 378/62 |
| 2014/0079310 A1* | 3/2014 | Nakatsugawa ........ A61B 6/542 382/132 |
| 2020/0311914 A1* | 10/2020 | Zaharchuk ............ G06T 3/4007 |
| 2021/0266445 A1* | 8/2021 | Miyake ................... H04N 5/32 |

FOREIGN PATENT DOCUMENTS

| | | | |
|---|---|---|---|
| JP | 2007082907 | A | 4/2007 |
| JP | 2007236804 | A | 9/2007 |
| JP | 2009297284 | A | 12/2009 |
| JP | 2013138828 | A | 7/2013 |

OTHER PUBLICATIONS

Notice of Allowance for corresponding U.S. Appl. No. 16/250,308; dated Feb. 10, 2021.
JPO Notice of Reasons for Refusal for corresponding JP Application No. 2018-194764; dated Aug. 23, 2022.

* cited by examiner

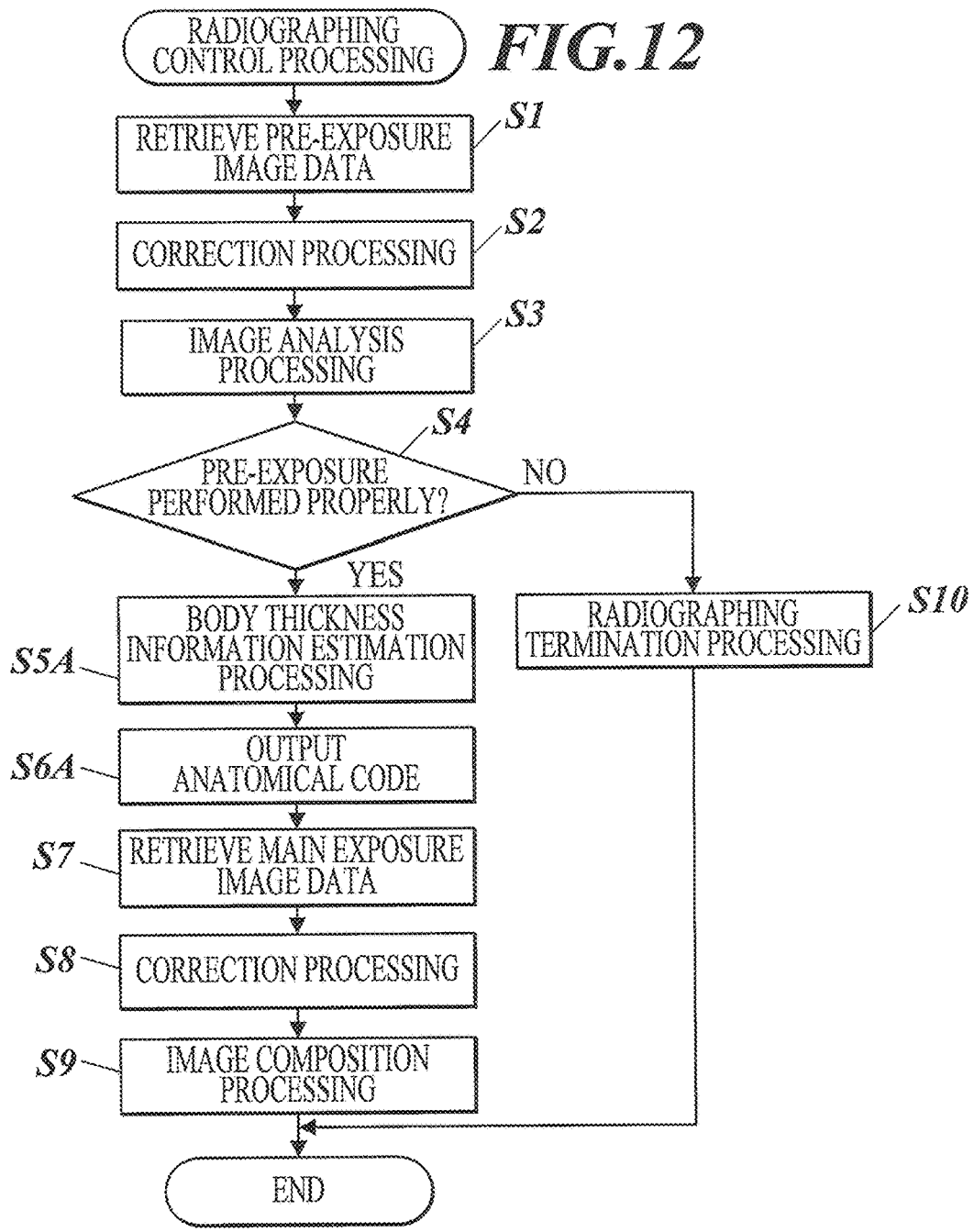

RADIOGRAPHING CONTROL APPARATUS, RADIOGRAPHIC IMAGING APPARATUS AND RADIOGRAPHIC IMAGING SYSTEM

CROSS-REFERENCE TO RELATED APPLICATION

The present application is a continuation application of U.S. patent application Ser. No. 16/250,308, filed on Jan. 17, 2019, the entire contents of which are incorporated herein by reference and priority to which is hereby claimed. The application Ser. No. 16/250,308 claimed the benefit of the date of the earlier filed Japanese Patent Application No. 2018-006819 filed on Jan. 19, 2018 and Japanese Application No. 2018-194764, filed on Oct. 16, 2018, priority to which is also claimed herein, the contents of which are also incorporated by reference herein.

BACKGROUND

1. Technological Field

The present invention relates to a radiographing control apparatus, a radiographic imaging apparatus and a radiographic imaging system.

2. Description of the Related Art

An automatic exposure controlling function for taking a radiographic image has been known in the art, which involves performing a pre-exposure at a lower dose than the dose of a subsequent main exposure and determining radiographing conditions such as the dose of the main exposure based on an obtained pre-exposure image and supplementary information associated with the pre-exposure image.

For example, JP 2007-236804A discloses an X-ray diagnostic apparatus for mammography that includes:
an X-ray exposing means;
an X-ray flat imaging device that detects X-ray emitted to a detector plane;
an image generating means that generates an X-ray image based on the detected X-ray;
a determining means that determines radiographing conditions based on the generated X-ray image; and
a controlling means that controls the X-ray exposing means to emit X-ray according to the determined radiographing conditions.

JP 2009-297284A discloses a radiographic imaging apparatus with a radiation source and a radiographic imaging apparatus, which includes:
an imaging unit that performs a pre-exposure and a main exposure;
a display that displays an image taken by the imaging unit in a browsable manner to a user;
a storage that stores an image;
an output unit that outputs an image; and
a controller that controls the radiographic imaging apparatus,
wherein the controller stores a pre-exposure image obtained by the pre-exposure in the storage and only outputs a main exposure image obtained by the main exposure to the output unit.

However, in the apparatus disclosed in JP 2007-236804A, not the pre-exposure image but the main exposure image is used to check whether a subject is in a proper position. Since it is difficult to make a diagnosis with a main exposure image that is radiographed in an improper position, it is sometimes necessary to retake a radiographic image. In this case, a subject is unnecessary exposed to extra radiation by one main exposure.

In the technique disclosed in JP 2009-297284A, a pre-exposure image is used for positioning a subject. That is, positioning of the subject for a main exposure is performed right before the main exposure, and whether the position is proper becomes clear after the main exposure. Therefore, there is a possibility that the main exposure is performed in an improper position, which requires to retake a radiographic image.

SUMMARY

The present invention has been made in view of the above-described problem, and an object thereof is to prevent a main exposure from being performed in an improper position when using a radiographic imaging system that determines the radiographing conditions of the main exposure based on a pre-exposure image obtained by a pre-exposure.

To achieve at least one of the abovementioned objects, according to an aspect of the present invention, a radiographing control apparatus includes a hardware processor which
retrieves image data of a subject from an external radiographic imaging apparatus, in which the radiographic imaging apparatus is exposed to a radiation from an external irradiating apparatus through the subject to generate the image data,
retrieves pre-exposure image data which the external radiographic imaging apparatus generates by performing a pre-exposure to the subject at a pre-exposure dose of less than a dose of a subsequent main exposure, and calculates a total dose required to obtain diagnostic image data to be used for diagnosis based on the pre-exposure image data,
outputs a main exposure dose based on the calculated total dose to the external irradiating apparatus and the external radiographic imaging apparatus, and
retrieves main exposure image data which the external radiographic imaging apparatus generates by performing the main exposure to the subject at the main exposure dose, and combines the main exposure image data with the pre-exposure image data to generate the diagnostic image data.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, and wherein:

FIG. 12 is a flowchart of radiographing control processing performed by the console of the radiographic imaging system according to the fourth embodiment of the present invention; and FIG. 13 illustrates examples of anatomical codes output from the console in FIG. 12.

DETAILED DESCRIPTION OF EMBODIMENTS

First Embodiment

Hereinafter, a first embodiment of the present invention will be described with FIG. 1 to FIG. 9. However, the scope of the present invention is not limited to the following embodiments, and suitable changes can be made within the features of the present invention.

While details of a subject to be radiographed is not described, the present invention is applicable to radiographing any part of a human body and to radiographing other subjects such as animals in addition to human beings.

Radiographic Imaging System

Figure 1:
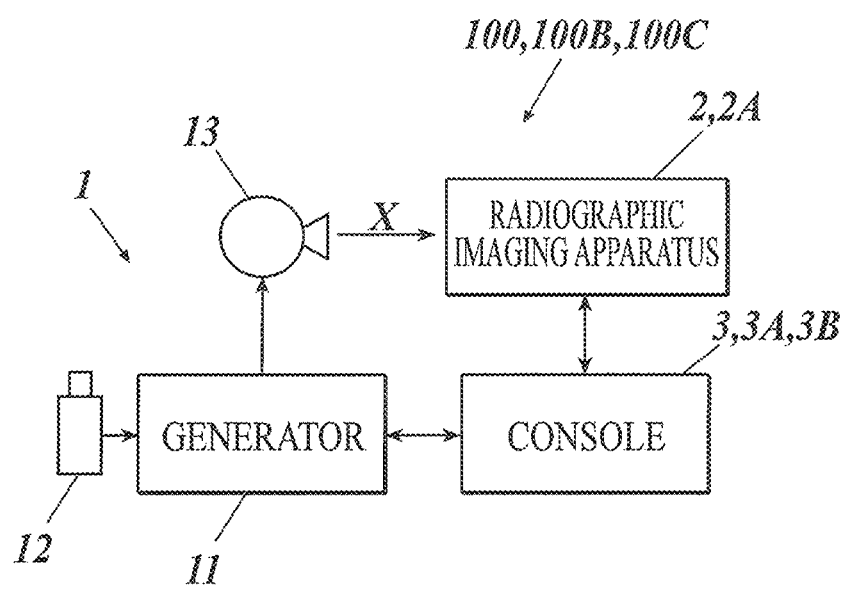
FIG. 1 is a block diagram of the configuration of a radiographic imaging system according to a first (or third or fourth) embodiment of the present invention.

First, the configuration of the radiographic imaging system according to the embodiment will be described. FIG. 1 is a block diagram of the radiographic imaging system 100. The reference signs in parentheses in FIG. 1 are those in third and fourth embodiments, which will be described later.

As illustrated in FIG. 1, the radiographic imaging system 100 of the embodiment includes an irradiating apparatus 1, a radiographic imaging apparatus 2 and a console 3.

The radiographic imaging system 100 is connectable to a radiography information system (RIS), a picture archiving and communication system (PACS) and the like (not shown).

The irradiating apparatus 1 is connected to the console 3 in a wired or wireless manner so that communication is possible.

The irradiating apparatus 1 includes a generator 11, an exposure switch 12 and a radiation source 13.

The generator 11 is configured to be able to apply a voltage to the radiation source 13 according to preset radiation radiographing conditions (tube voltage, tube current, irradiation time (mAs), etc.) in response to a user operation on the exposure switch 12.

The radiation source 13 (tube) includes a rotating anode, a filament and the like (not shown). When a voltage is applied by the generator 11, the filament emits an electron beam to the rotating anode according to the applied voltage, and the rotating anode generates a radiation X (X-ray or the like) at a dose corresponding to the intensity of the electron beam.

In FIG. 1, the components 11 to 13 are illustrated as separate components. However, they may be integrated as a single component.

In FIG. 1, the exposure switch 12 is connected to the generator 11. However, the exposure switch 12 may be incorporated in another device (e.g. an operation console (not shown)).

Further, the irradiating apparatus 1 may be either installed in an X-ray room or configured as a movable apparatus that is incorporated in a visiting car or the like.

The radiographic imaging apparatus 2 is connected to the console 3 in a wired or wireless manner so that communication is possible.

The radiographic imaging apparatus 2 is configured to be exposed to the radiation X from the irradiating apparatus 1 through a subject so as to be able to generate an image data of the subject.

The details of the radiographic imaging apparatus 2 will be described later.

The console 3, which is constituted by a PC, a portable terminal or a dedicated device, is connected to the irradiating apparatus 1, the radiographic imaging apparatus 2 and the like in a wired or wireless manner so that communication is possible.

The console 3 is capable of setting the radiographing conditions of the irradiating apparatus 1 and the radiographic imaging apparatus 2, a part to be radiographed and the like according to a radiographing order from an external device (RIS or the like) or a user operation.

Details of the console 3 will be described later.

Configuration of Radiographic Imaging Apparatus

Figure 2:
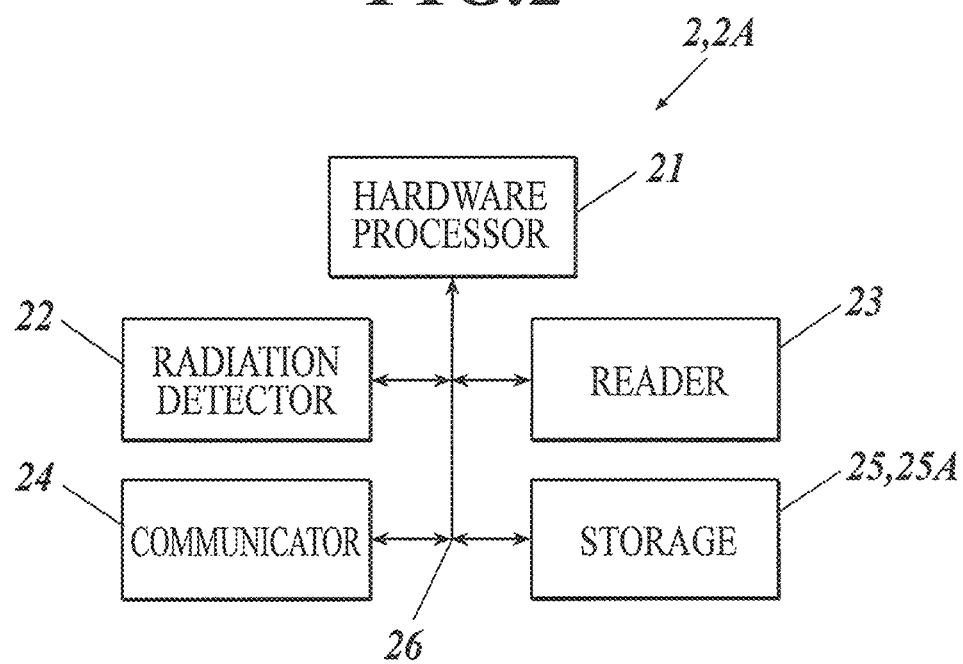
FIG. 2 is a block diagram of the specific configuration of a radiographic imaging apparatus of the radiographic imaging system in FIG. 1.

Details of the radiographic imaging apparatus 2 of the radiographic imaging system 100 will be described. FIG. 2 is a block diagram of the specific configuration of the radiographic imaging apparatus 2. The reference signs in parentheses in FIG. 2 are denoted for the third embodiment, which will be described later.

As illustrated in FIG. 2, the radiographic imaging apparatus 2 includes a hardware processor 21, a radiation detector 22, a reader 23, a communicator 24, a storage 25, and a bus 26 connecting the components 21 to 25 with each other.

The hardware processor 21 includes a CPU (Central Processing Unit), a RAM (Random Access Memory) and the like.

In response to a control signal received from an external device such as the console 3, the CPU of the hardware processor 21 reads a variety of programs stored in the storage 25, develops them in the RAM and performs a variety of processing according to the developed programs so as to integrally control the components of the radiographic imaging apparatuses 2.

The radiation detector 22 is constituted by a substrate on which pixels, each including a radiation detecting element that receives the radiation X to generate a charge according to the dose and a switching element, are arranged two-dimensionally (in a matrix).

The reader 23 is configured to be able to read the amount of charges released from the pixels as signal values and to generate image data from the signal values.

The communicator 24 is configured to be able to receive various control signals, various data and the like from an external device and to send various control signals, the generated image data and the like to the external device.

The storage 25 is constituted by a non-volatile semiconductor memory, a hard disk or the like, in which a variety of programs to be executed by the hardware processor 21, parameters required to perform the processing according to the programs and the like are stored.

The storage 25 is capable of storing the image data generated by the reader 23 and various data processed by the hardware processor 21.

In the radiographic imaging apparatus 2 having the above-described configuration, when the radiation detector 22 is exposed to a radiation in a state in which the switching elements are turned off by the hardware processor 21, it accumulates charges in the pixels according to the dose of the radiation. Then, the hardware processor 21 turns on the switching elements to release the charges in the pixels, and the reader 23 converts the amount of charges to signal values to generate image data. That is, the hardware processor 21, the radiation detector 22 and the reader 23 of the radiographic imaging apparatus 2 serve as an image generating means of the present invention.

The radiographic imaging apparatus 2 may include a scintillator or the like and convert the radiation X to light of a different wavelength such as visible light by using the scintillator to generate charges according to the converted light (so-called indirect type). Alternatively, the radiographic imaging apparatus 2 may generate charges directly from the radiation X without using any scintillator or the like (so-called direct type).

Further, the radiographic imaging apparatus 2 may be configured as a dedicated apparatus integrated with a radiographic table or a portable apparatus (cassette).

Configuration of Console

Figure 3:
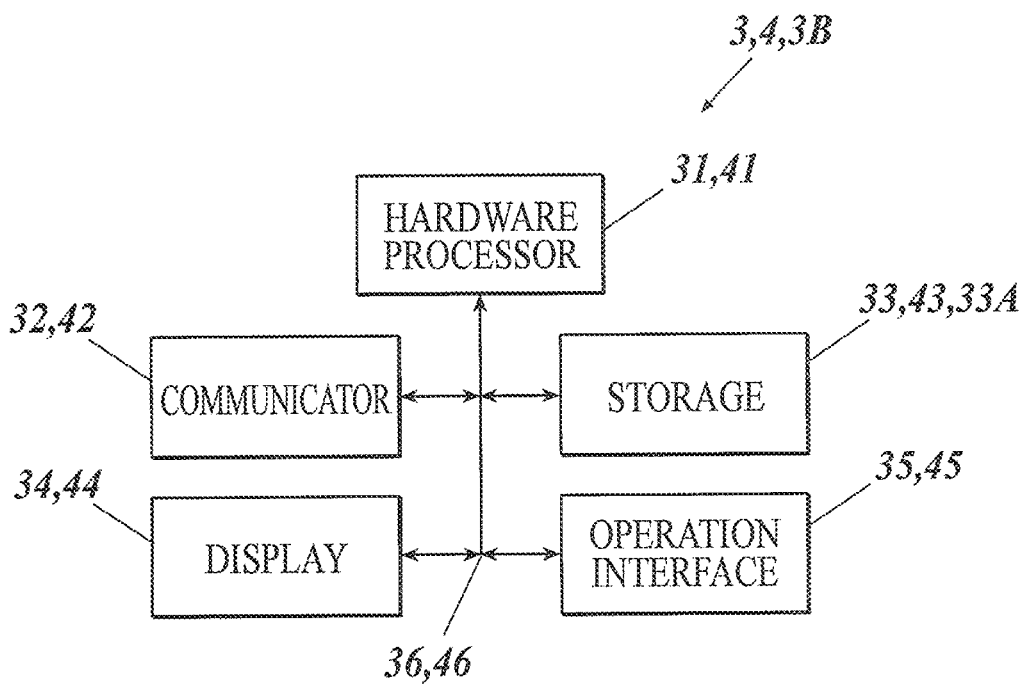
FIG. 3 is a block diagram of the specific configuration of a console of the radiographic imaging system according to the first embodiment (a radiographing control apparatus of a radiographic imaging system according to a second embodiment, a console of the radiographic imaging system according to the fourth embodiment)

Details of the console 3 of the radiographic imaging system 100 will be described. FIG. 3 is a block diagram of the specific configuration of the console 3. The reference signs in parentheses in FIG. 3 are denoted for the second and fourth embodiments, which will be described later.

As illustrated in FIG. 3, the console 3 includes a hardware processor 31, a communicator 32, a storage 33, a display 34, an operation interface 35, and a bus 36 connecting the components 31 to 35 with each other.

The hardware processor 31 is constituted by a CPU (Central Processing Unit), a RAM (Random Access Memory) and the like. In response to a user operation on the operation interface 35, the CPU of the hardware processor 31 reads a variety of programs stored in the storage 33, develops them in the RAM and performs a variety of processing according to the developed programs so as to integrally control the operation of the components of the console 3.

The communicator 32, which includes a LAN adapter, a modem, a TA (Terminal Adapter) and the like, controls transmission and reception of data to and from a device connected to a communication network.

The storage 33 is constituted by a non-volatile semiconductor memory, a hard disk or the like, in which a variety of programs to be executed by the hardware processor 31 (including a program for performing radiographing control processing (described later)), parameters required to perform processing according to the programs and the like are stored.

The storage 33 can store image data received from the radiographic imaging apparatus 2 or image data processed by the hardware processor 31 along with supplementary information.

The display 34, which is constituted by an LCD (Liquid Crystal Display), a CRT (Cathode Ray Tube) or the like, displays a user instruction input on the operation interface 35, data and the like according to a display signal input from the hardware processor 31.

The operation interface 35, which is constituted by a keyboard with cursor keys, number keys, various functional keys and the like and a pointing device such as a mouse, receives a user instruction as a key operation on the keyboard or a mouse operation and outputs the instruction signal to the hardware processor 31.

The operation interface 35 may include a touch panel disposed on the display area of the display 34. In this case, the operation interface 35 receives a user instruction as an input on the touch panel and outputs the instruction signal to the hardware processor 31.

Radiographing Control Processing

Figure 4:
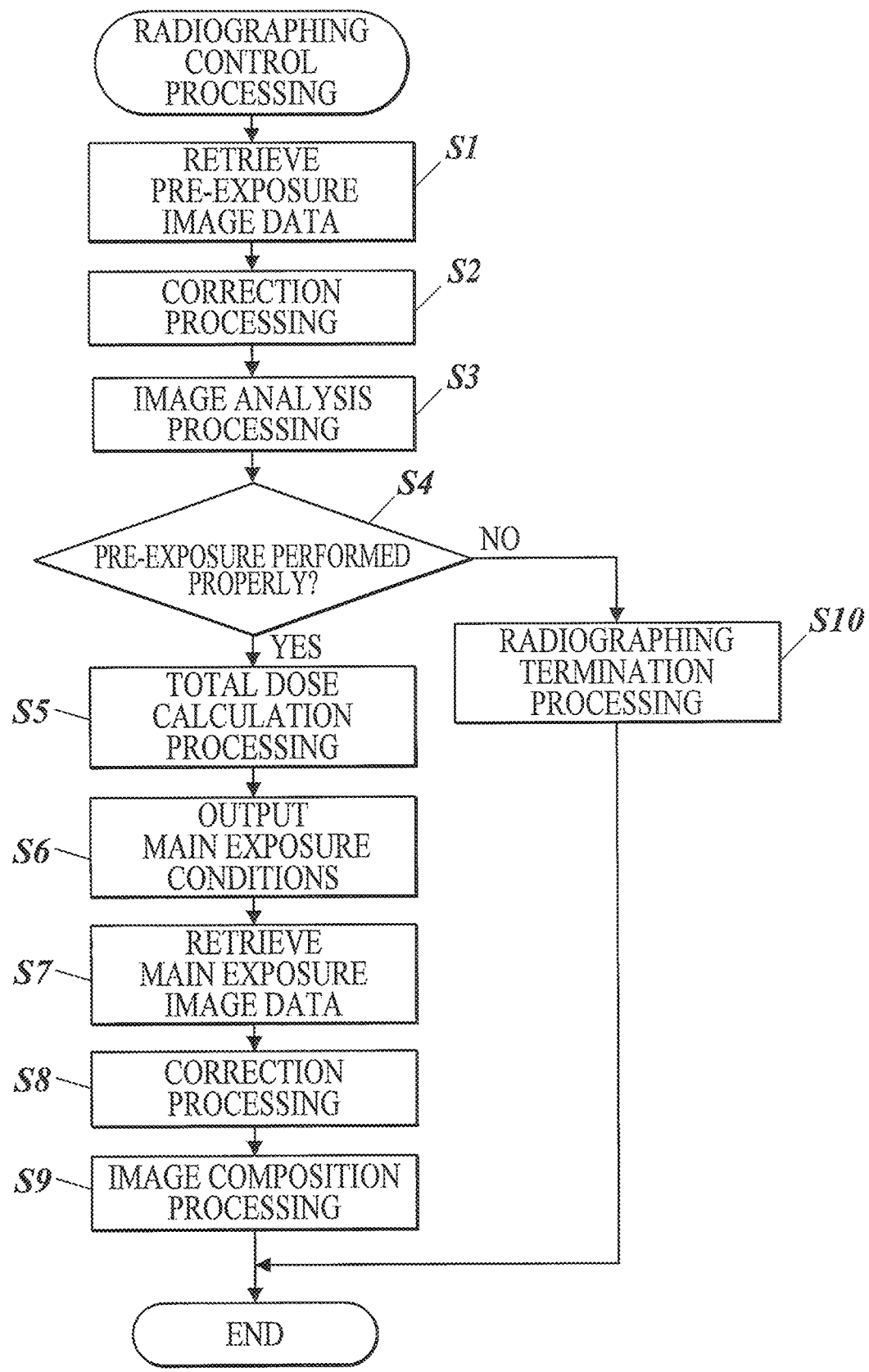
FIG. 4 is a flowchart of radiographing control processing performed by the console in FIG. 3.
Figure 5:
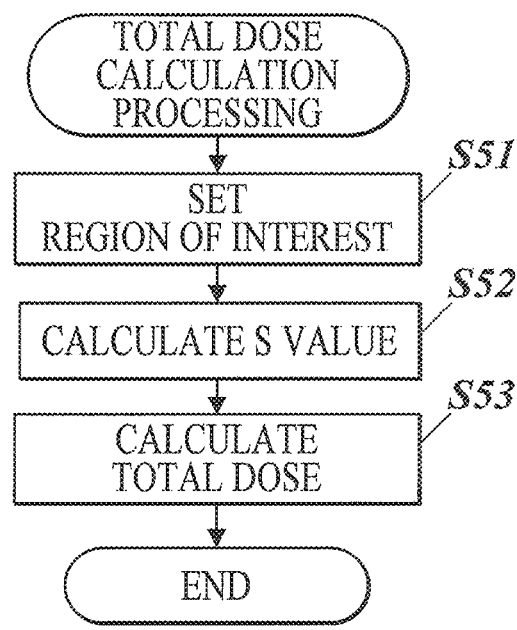
FIG. 5 is a flowchart of total dose calculation processing in the radiographing control processing in FIG. 4.
Figure 6:
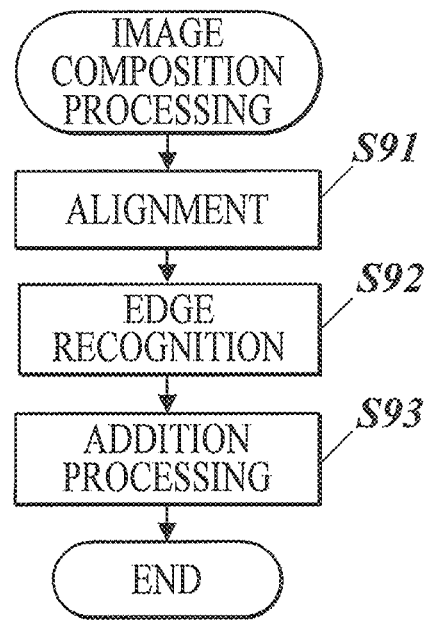
FIG. 6 is a flowchart of image composition processing in the radiographing control processing in FIG. 4.

Details of the radiographing control processing, which is one of processing performed by the console 3, will be described. FIG. 4 is a flowchart of the radiographing control processing performed by the console 3, FIG. 5 is a flowchart of total dose calculation processing in the radiographing control processing in FIG. 4, and FIG. 6 is a flowchart of image composition processing in the radiographing control processing in FIG. 4.

The hardware processor 31 of the console 3 of the embodiment starts the radiographing control processing when a predetermined starting condition is satisfied, e.g. when a starting operation is made on the operation interface 35, the exposure switch 12 is pressed, the irradiating apparatus 1 or the radiographic imaging apparatus 2 performs a radiographing operation, image data is received from the radiographic imaging apparatus 2, or the like.

Specifically, as illustrated in FIG. 4, the hardware processor 31 firstly retrieves pre-exposure image data which the radiographic imaging apparatus 2 has generated by performing a pre-exposure to a subject at a pre-exposure dose that is lower than the dose of the subsequent main exposure (Step S1). Along with the pre-exposure image data, the hardware processor 31 also obtains supplementary information associated with the pre-exposure image data.

The supplementary information includes the pre-exposure dose of the pre-exposure, which is calculated from the tube voltage, the tube current and the irradiation time, the part to be radiographed and the like.

The hardware processor 31 and the communicator 32 that perform this step serve as an image retrieving means of the present invention.

It is preferred that the pre-exposure image data and the supplementary information are received via the communicator 32 in a wired or wireless manner. However, they may also be received via a medium such as a USB memory.

To obtain the data, the console 3 may request data transmission by sending a signal representing a request of data transmission to the radiographic imaging apparatus 2. Alternatively, the console 3 may wait (repeat Step S1) until the radiographic imaging apparatus 2 transmits the data.

After retrieving the pre-exposure image data, the hardware processor 31 performs correction processing (Step S2). Specifically, the hardware processor 31 performs an offset correction on the pre-exposure image data retrieved in Step S1.

It is preferred that an offset data (dark image data) for the offset correction is obtained before performing the pre-exposure.

In this step, the hardware processor 31 may perform an additional correction (e.g. logit transformation or the like).

When the radiographic imaging apparatus 2 has a function of performing the above-described correction processing on the generated image data, Step S2 is not necessary. In this case, the radiographic imaging apparatus 2 performs the offset correction after the pre-exposure, and the hardware processor 2 retrieves the corrected pre-exposure image data in Step S1.

Then, the hardware processor 31 performs image analysis processing (Step S3). Specifically, the hardware processor 31 analyzes the pre-exposure image data and the supplementary information associated with the pre-exposure image data about whether there is an abnormality in the pre-exposure image. For example, the part to be radiographed (lung field, KUB, etc.) is not fully shown, an artificial object (a stripe pattern due to misalignment of a grid or the like) is shown, etc.

To determine whether the part to be radiographed is fully shown, for example, a technique disclosed in JP 2011-255061A can be used. Specifically, a specified radiation field is divided into small areas, the feature amount is extracted from small areas at the boundary of the radiation field, and it is determined whether a part to be radiographed crosses over the boundary of the radiation field based on the arrangement of the feature amounts.

When the same part of the same subject was radiographed in the past, the determination may be made based on a comparison with the old image. In this case, a difference from the old image due to a difference in the incident angle of radiation is also counted as an abnormality when the difference is too large to make a comparison.

Then, the hardware processor 31 makes a determination as to whether the pre-exposure has been properly performed (Step S4). Specifically, the hardware processor 31 makes a determination as to whether there is an abnormality as described above in the pre-exposure image based on the result of the image analysis processing in Step S3.

If it is determined that there is no abnormality, i.e. the pre-exposure has been properly performed (Step S4, Yes), the hardware processor then performs various processing for the main exposure (Step S5 to Step S9). These steps will be described later.

If it is determined that there is an abnormality, i.e. the pre-exposure has not been properly performed (Step S4, No), the hardware processor 31 performs radiographing termination processing (Step S10), and the radiographing control processing ends.

The radiographing termination processing in Step S10 includes stopping the operation of the irradiating apparatus 1 and the radiographic imaging apparatus 2, giving a user a warning to cancel the main exposure (displays a message or the like on the display 34 or outputs a sound) and the like.

The hardware processor 31 that carries out Step S3 and Step S4 serves as a radiographing determining means of the present invention. That is, before performing the main exposure having a high dose, the hardware processor 31 can make a determination as to whether the subject is in a proper position (whether it is necessary to retake a radiographic image) based on the pre-exposure image. This can prevent the main exposure from being performed in an improper position and thereby prevent a subject from being unnecessarily exposed to a radiation.

When the pre-exposure is properly performed, the user can perform the main exposure without checking the pre-exposure image. This can reduce the burden on the user in the radiographing process.

When the pre-exposure is not properly performed, another pre-exposure is performed again. However, the dose of a pre-exposure is lower than the dose of a main exposure, it is possible to reduce the exposure dose compared to a conventional process in which a main exposure is performed again.

In Step S3, the user may be asked to manually analyze the pre-exposure image instead of the automatic analysis of the pre-exposure image data. In this case, Step S3 is omitted, and the result of the analysis by the user is received in Step S4.

After Step S10, a step of making a determination as to whether a predetermined condition is satisfied (e.g. whether a user operation to resume radiographing is made, or the like) may be added. If the predetermined condition is satisfied, the process returns to Step S5 and the subsequent steps.

After Step S4, the pre-exposure image may be displayed on the display 34.

In this regard, a reduced image of the pre-exposure image, which has a lower resolution, may be displayed.

However, it is not necessary to always display the pre-exposure image. The console 3 may be configured such that the user can select whether to display the pre-exposure image or designate a condition for displaying the pre-exposure image. In this configuration, it is possible to configure the console 3 to display the pre-exposure image only when it is necessary for the user to check the pre-exposure image, e.g. when it is determined that the subject is not in a proper position. This improves convenience of users.

If it is determined in Step S4 that the pre-exposure has been properly performed (Step S4, Yes), the hardware processor 31 performs total dose calculation processing (Step S5). This processing involves calculating a total dose required to obtain diagnostic image data to be used for diagnosis based on the pre-exposure image data and the supplementary information associated with the pre-exposure image data.

To calculate the total dose, for example, a technique as disclosed in WO 2006/62013A can be used. Specifically, a region of interest (ROI) is set in the pre-exposure image as illustrated in FIG. 5 (Step S51).

Then, the S value (sensitivity) is calculated (Step S52). In this step, a histogram of the signal values of pixels in the region of interest is generated, and the median value of the dynamic range of the histogram is determined. This median value is the S value.

Then, the total dose is calculated (Step S53). Dose of radiographing is inversely proportional to S value. Based on this relationship, a dose is calculated from a target S value preset by a manufacturer or the user so that the S value of a radiographic image obtained after the subsequent exposure is equal to the target S value. The dose thus calculated is the total dose.

The hardware processor 31 that performs this processing serves as a total dose calculating means of the present invention.

After calculating the total dose, the hardware processor 31 outputs main radiographing conditions as illustrated in FIG. 4 (Step S6). In this step, the hardware processor 31 outputs a main exposure dose as a main radiographing condition, which is based on the total dose calculated in Step S2, to the irradiating apparatus 1 and the radiographic imaging apparatus 2.

The main exposure dose may be either equal to the total dose or obtained from the total dose through a predetermined calculation.

In the embodiment, the hardware processor 31 also outputs, for example, a part to be radiographed, the thickness of a body, a radiographing direction and the like as the main radiographing conditions in addition to the main exposure dose.

The hardware processor 31 that performs this step serves as a dose outputting means of the present invention.

In outputting the main radiographing conditions (Step S6), the value obtained by subtracting the pre-exposure dose from the calculated total dose may be output as the main exposure dose.

A conventional automatic exposure controlling function suffers from an increase of the total dose by the dose of a pre-exposure compared to a normal radiographing process without the function. In contrast, in the embodiment, the sum of the dose of the pre-exposure and the dose of the main exposure is equal to the dose of a conventional main exposure. Therefore, it is possible to obtain a diagnostic image without increasing the dose compared to a conventional process of taking a radiographic diagnostic image.

In outputting the main radiographing conditions (Step S6), the tube voltage, the values of tube current and the irradiation time required for generating a radiation at the main exposure dose may be output instead of directly outputting the value of the main exposure dose.

After the output of the main radiographing conditions before Step S7, the irradiating apparatus 1 performs the main exposure to the subject at the main exposure dose, and the radiographic imaging apparatus 2 generates main exposure image data.

After the radiographic imaging apparatus 2 generates the main exposure image data, the hardware processor 31 retrieves the main exposure image data generated by the radiographic imaging apparatus 2.

The specific process of retrieving the main exposure image data (Step S7) is the same as the above-described process of retrieving the pre-exposure image data (Step S1).

After retrieving the main exposure image data, the hardware processor 31 performs correction processing (Step S8). Specifically, the hardware processor 31 performs an offset correction on the main exposure image data.

It is preferred that offset data to be used for the offset correction of the main exposure image data is obtained immediately before or immediately after the main exposure.

In this step, the hardware processor 31 may perform an additional correction, e.g. logit transformation or the like.

When the radiographic imaging apparatus 2 has a function of performing the above-described correction processing on the generated image data, Step S8 is not necessary as with Step S2.

Then, the hardware processor 31 performs image composition processing (Step S9). In this step, the hardware processor 31 generates the diagnostic image data by combining the main exposure image data, which is generated by the radiographic imaging apparatus 2 as a result of the main exposure at the main exposure dose, with the pre-exposure image data.

To combine the images, for example, a technique as disclosed in JP 2015-092913A can be used. Specifically, as illustrated in FIG. 6, the main exposure image is aligned with the pre-exposure image (Step S91). In this step, one of the images is shifted so that the contours of the subject in the images overlap each other.

Then, the edges of the images are recognized (Step S92).

Then, addition processing (Step S93) is performed. In this step, the main exposure image data is combined with the pre-exposure image data so that the diagnostic image data is generated. Specifically, the signal values of the pixels of the pre-exposure image data are added to the signal values of the corresponding pixels of the main exposure image data.

In the embodiment, the signal values of the pre-exposure image data are not simply added to the signal values of the main exposure image data. Instead, the signal values of the pre-exposure image data are relatively decreased in an edge area (or the signal values are relatively increased in a flat area other than the edge area). Specifically, for example, the following addition formula (1) may be used for the addition.

$$I_{(x,y)} = \{\beta_{(x,y)} \times I_{pre(x,y)} + I_{post(x,y)}\} / \{1 + \beta_{(x,y)}\} \quad (1)$$

$I_{(x,y)}$: the signal value of a pixel at a coordinate (x,y) after the addition (diagnostic image)

$\beta_{(x,y)}$: an addition coefficient applied to the pixel at the coordinate (x,y)

$I_{pre(x,y)}$: the signal value of a pixel at the coordinate (x,y) of the pre-exposure image $I_{post(x,y)}$: the signal value of a pixel at the coordinate (x,y) of the main exposure image The coordinate (x,y) are a coordinate after the alignment.

The values of $\beta$ may be $0<\beta<1$ at coordinates in the edge area and $\beta=1$ at coordinates in the flat area. Alternatively, the values of $\beta$ may be $\beta=1$ at coordinates in the edge area and $1<\beta$ at coordinates in the flat area. Yet alternatively, the value of $\beta$ may be $0<\beta<1$ at coordinates in the edge area and $1<\beta$ at coordinates in the flat area.

It is preferred that the values of $\beta$ for the respective coordinates (x,y) are precalculated in Step S92.

While it is possible to align the contour of the radiographed part in the pre-exposure image with the contour of the radiographed part in the main exposure image, the edges are not often congruent with each other due to rotation and twist of the radiographed part. Adding the signal values in the above-described manner weakens the edge of the pre-exposure image. This can prevent the edge of the diagnostic image from being blurred due to misalignment between the main exposure image and the pre-exposure image.

The hardware processor 31 that performs Step S9 serves as an image compositing means of the present invention. Since the diagnostic image data is generated by combining the pre-exposure image data with the main exposure image data, the image quality (S/N) of the diagnostic image is not deteriorated even when the main exposure is performed at a decreased dose.

The image composition processing may be performed before the correction processing (Step S8).

When it is possible to take the radiographic images in a condition free from misalignment of the edge between the pre-exposure and the main exposure, e.g. a jig is used to fix the part to be radiographed, Step S92 is not necessary. In Step S93, the signal values of the pre-exposure image are simply added to the signal values of the main exposure image.

In the image composition processing, it is preferred that the movement of the subject between the pre-exposure and the main exposure is measured on a segment basis based on the pre-exposure image data and main exposure image data. Then, the signal values of the pre-exposure image data are relatively enhanced in segments where the movement is small while the signal values are not added in segments where the movement is larger than a predetermined value.

Specifically, the images are divided into small segments, and the movement is measured in each of the segments.

The hardware processor 31 that performs the above-described processing serves as a movement measuring means of the present invention. Even when the subject moves his/her body between the pre-exposure and the main exposure, it is possible to prevent the diagnostic image from being blurred as a result of the composition.

This is the flow of the radiographing control processing.

The console 3 of the embodiment that performs the radiographing control processing serves as the radiographing control apparatus of the present invention.

The console 3 may have a function of controlling the irradiation. Specifically, the console 3 may be configured to output to the irradiating apparatus 1 an exposure permission signal representing permission/prohibition of irradiation as on/off (unlock/lock). The console 3 switches the exposure permission signal between on and off at the timing according to the pre-radiographing conditions and the main radiographing conditions.

This processing may be performed in the above-described radiographing control processing (between Step S1 and Step S2 and between Step S6 and Step S7) or as a separate processing from the radiographing control processing.

Flow of Radiographing

Figure 7:
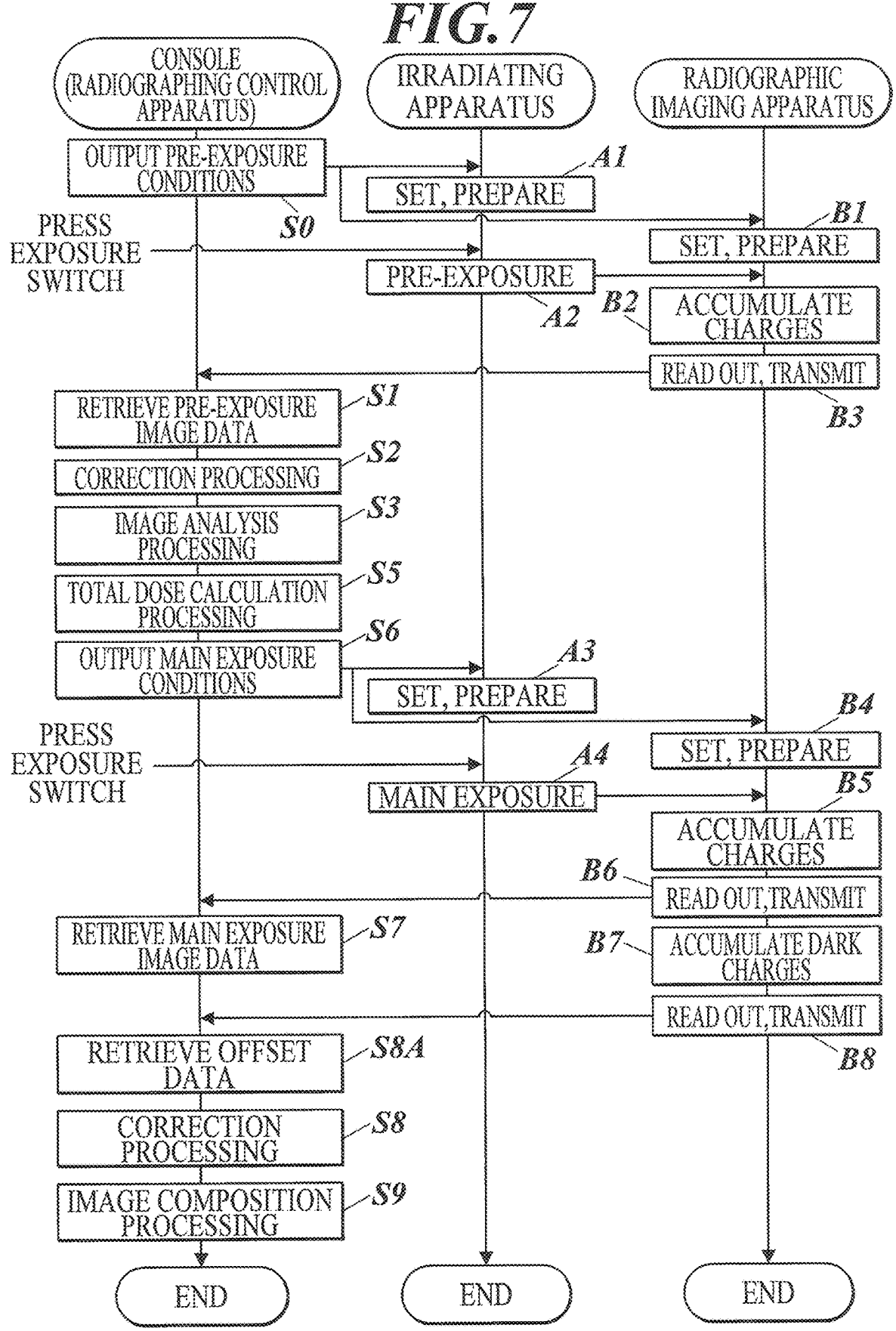
FIG. 7 is a ladder chart of an operation of the radiographic imaging system according to the first embodiment.

The operation of the radiographic imaging system 100 will be described. FIG. 7 is a ladder chart illustrating a radiographing operation of the radiographic imaging system 100.

A process of taking a radiographic image of a subject with the radiographic imaging system 100 of the embodiment will be described. First, in response to a user input of pre-radiographing conditions on the console 3, the console 3 outputs the input pre-radiographing conditions to the irradiating apparatus 1 and the radiographic imaging apparatus 2 as illustrated in FIG. 7 (Step S0).

When the pre-radiographing conditions are input, the irradiating apparatus 1 and the radiographic imaging apparatus 2 set their own radiographing conditions to the pre-radiographing conditions so as to prepare for the pre-exposure at the pre-exposure dose (Step A1, Step B1).

Thereafter, when the user presses the exposure switch 12, the irradiating apparatus 1 exposes the subject and the radiographic imaging apparatus 2 behind the subject to a radiation at the pre-exposure dose (Step S2).

When exposed to the radiation, the radiographic imaging apparatus 2 accumulates charges in the pixels, which are generated by the radiation detecting elements according to the dose of the radiation (Step B2). The radiographic imaging apparatus 2 then converts the charges of the pixels to signal values to read them as the pre-exposure image data and sends the pre-exposure image data to the console 3 (Step B3).

After obtaining the pre-exposure image data (Step S1), the console 3 performs the correction processing on the received pre-exposure image data (Step S2).

Then, the console 3 performs the image analysis processing on the corrected pre-exposure image data (Step S3). If the analysis result does not indicate any abnormality, the console 3 performs the total dose calculation processing (Step S5) and outputs to the irradiating apparatus 1 and the radiographic imaging apparatus 2 the main radiographing conditions including the main exposure dose based on the calculated total dose (Step S6).

When the main radiographing conditions are input, the irradiating apparatus 1 and the radiographic imaging apparatus 2 set their own radiographing conditions to the main radiographing conditions so as to prepare for the main exposure at the main exposure dose (Step A3, Step B4).

Thereafter, when the user presses the exposure switch 12, the irradiating apparatus 1 exposes the subject and the radiographic imaging apparatus 2 behind the subject to a radiation at the main exposure dose.

When exposed to the radiation, the radiographic imaging apparatus 2 accumulates charges in the pixels, which are generated by the radiation detecting elements according to the dose of the radiation (Step B5). The radiographic imaging apparatus 2 then converts the charges in the pixels to signal values to read them as the main exposure image data and sends the main exposure image data to the console 3 (Step B6).

Immediately before or after Step B5 and Step B6 (immediately after Step B5 and Step B6 in the example in FIG. 7), the radiographic imaging apparatus 2 accumulates dark charges in the pixels (Step B7), converts the dark charges in the pixels to signal values to read them as offset data, and sends the offset data to the console 3 (Step B8).

After obtaining the main exposure image data and the offset data (Step S7, Step S8A), the console 3 performs the correction processing on the received main exposure image data (Step S8).

Then, the console 3 performs the image composition processing on the corrected main exposure image data using the corrected pre-exposure image data (Step S9).

The diagnostic image data is thus generated, and the radiographing operation ends.

Figure 8:
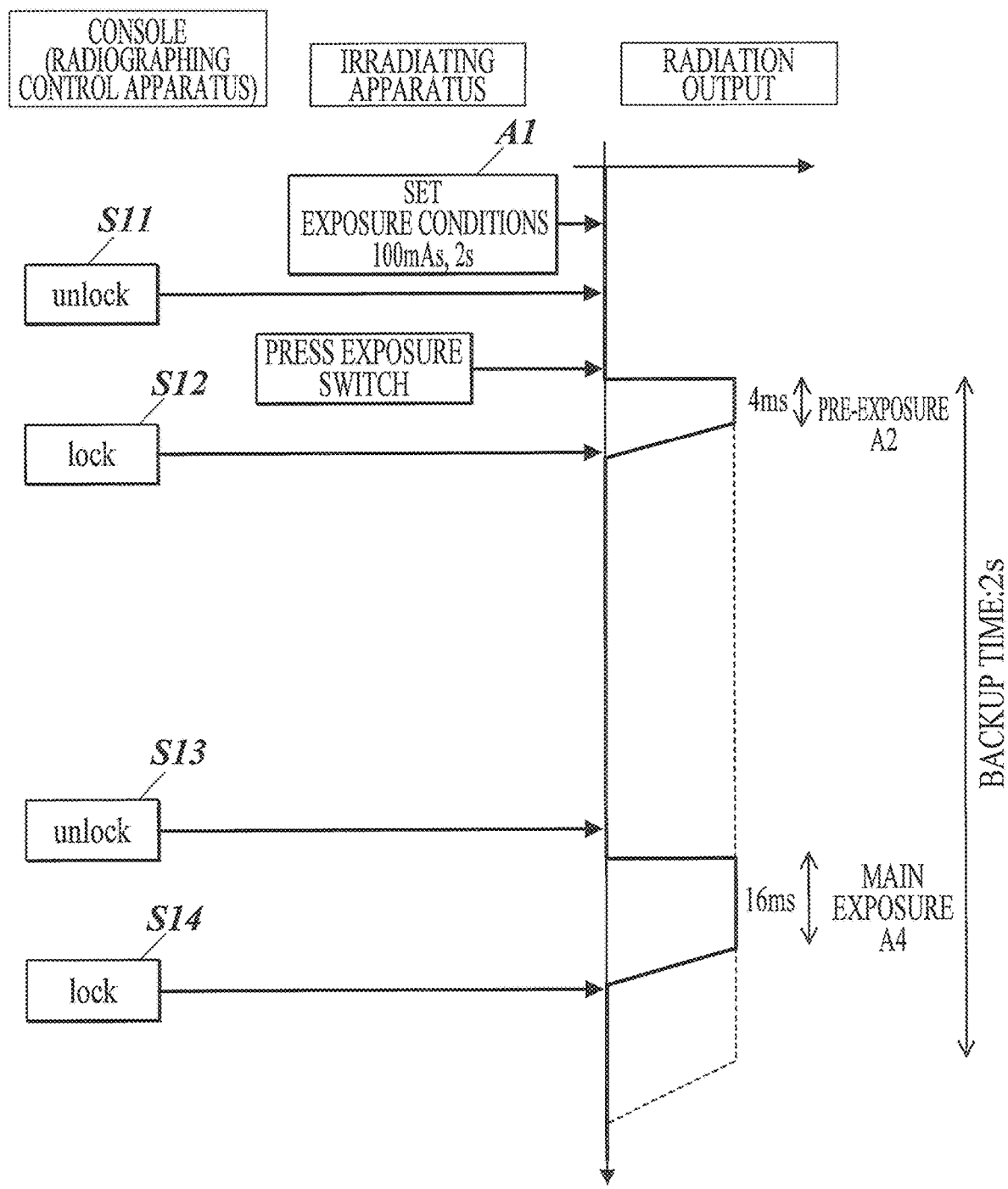
FIG. 8 is a timing chart of another operation of the radiographic imaging system according to the first embodiment.
Figure 9:
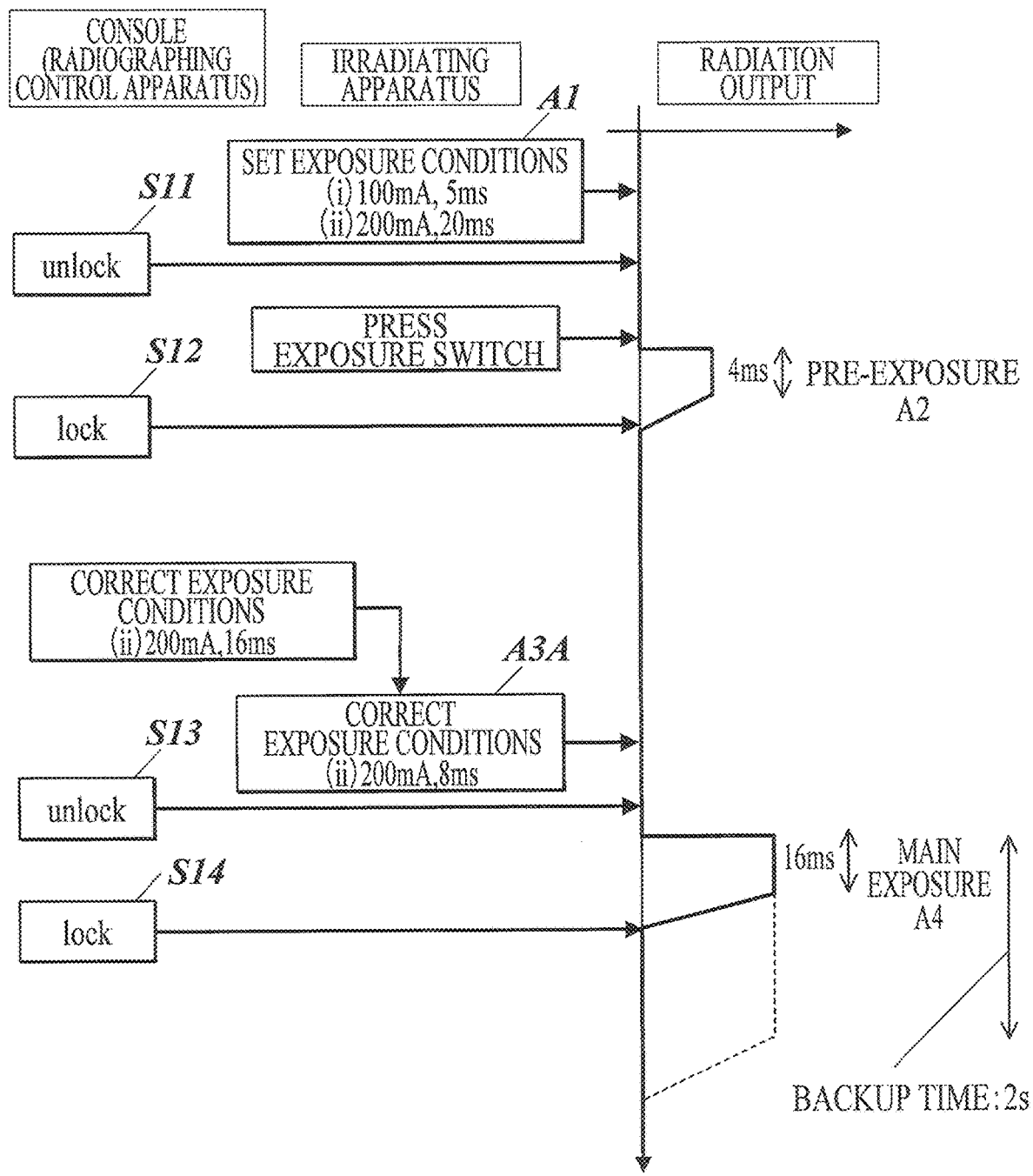
FIG. 9 is a timing chart of another operation of the radiographic imaging system according to the first embodiment.

When the console 3 has the above-described function of controlling the irradiation, the console 3 and the irradiating apparatus 1 operate, for example, as illustrated in FIG. 8 and FIG. 9 in the above-described flow of the radiographing process.

For example, FIG. 8 illustrates the case in which a combination of the pre-exposure and the main exposure is regarded as a single exposure. After the pre-photographing conditions (a mAs value and a backup time or a time limit from the start to the end of the exposure) are set in the irradiating apparatus 1 (Step A1), the irradiating apparatus 1 sends to the console 3 a signal representing that the pre-photographing conditions have been set.

When receiving the signal representing that the pre-radiographing conditions have been set, the console 3 switches the exposure permission signal to ON (unlock) (Step S11).

When the user presses the exposure switch 12, the irradiating apparatus 1 sends to the console 3 a signal representing that the exposure switch 12 has been pressed. Further, the irradiating apparatus 1 exposes the subject and the radiographic imaging apparatus 2 behind the subject to a radiation at the pre-exposure dose (Step A2).

When receiving the signal representing the exposure switch 12 has been pressed, the console 3 starts a timer. After the elapse of a preset pre-exposure time, the console 3 switches the exposure permission signal to OFF (lock) (Step S12). Then, the irradiating apparatus 1 stops the radiation.

In a predetermined time from switching the exposure permission signal to OFF, the console 3 outputs the main radiographing conditions to the irradiating apparatus 1 (Step S6), and the irradiating apparatus 1 sets its own radiographing conditions to the main radiographing conditions (Step A3). When the predetermined time has elapsed, the console 3 switches the exposure permission signal to ON again (Step S13). Then, the irradiating apparatus 1 exposes the subject and the radiographic imaging apparatus 2 behind the subject to a radiation at the main exposure dose (A4).

When a preset main exposure time has elapsed since switching the exposure permission signal to ON, the console 3 switches the exposure permission signal to OFF again (Step S14). Then, the irradiating apparatus 1 stops the radiation.

FIG. 9 illustrates the case in which the pre-exposure and the main exposure are each regarded as a single exposure. In this case, the irradiating apparatus 1 sets its own radiographing conditions to the main radiographing conditions as well as the pre-radiographing conditions (Step A1). Then, the irradiating apparatus 1 sends to the console 3 a signal representing that the radiographing conditions have been set.

When receiving the signal representing the conditions have been set, the console 3 switches the exposure permission signal to ON (unlock) (Step S11).

When the user presses the exposure switch 12 in this state, the irradiating apparatus 1 sends to the console 3 a signal representing the exposure switch 12 has been pressed. Further, the irradiating apparatus 1 exposes the subject and the radiographic imaging apparatus 2 behind the subject to a radiation at the pre-exposure dose (Step A2).

When receiving the signal representing the exposure switch 12 has been pressed, the console 3 starts a timer. When a preset pre-exposure time has elapsed, the console 3 switches the exposure permission signal to OFF (lock) (Step S12). Then, the irradiating apparatus 1 stops the radiation.

In a predetermined time from switching the exposure permission signal to OFF, the console 3 performs the image analysis processing (Step S3). If it is determined that a correction to the main radiographing conditions is necessary, the console 3 sends a signal representing an instruction to make the correction to the irradiating apparatus 1.

When receiving the signal representing the instruction to make the correction, the irradiating apparatus 1 corrects the main radiographing conditions (Step A3A). When the predetermined time has elapsed, the console 3 switches the exposure permission signal to ON again (Step S13). Then, the irradiating apparatus 1 exposes the subject and the radiographic imaging apparatus 2 behind the subject to a radiation at the main exposure dose (A4).

When the predetermined main exposure time has elapsed since switching the exposure permission signal to ON, the console 3 switches the exposure permission signal to OFF again (Step S14). Then, the irradiating apparatus 1 stops the radiation.

Second Embodiment

Figure 10:
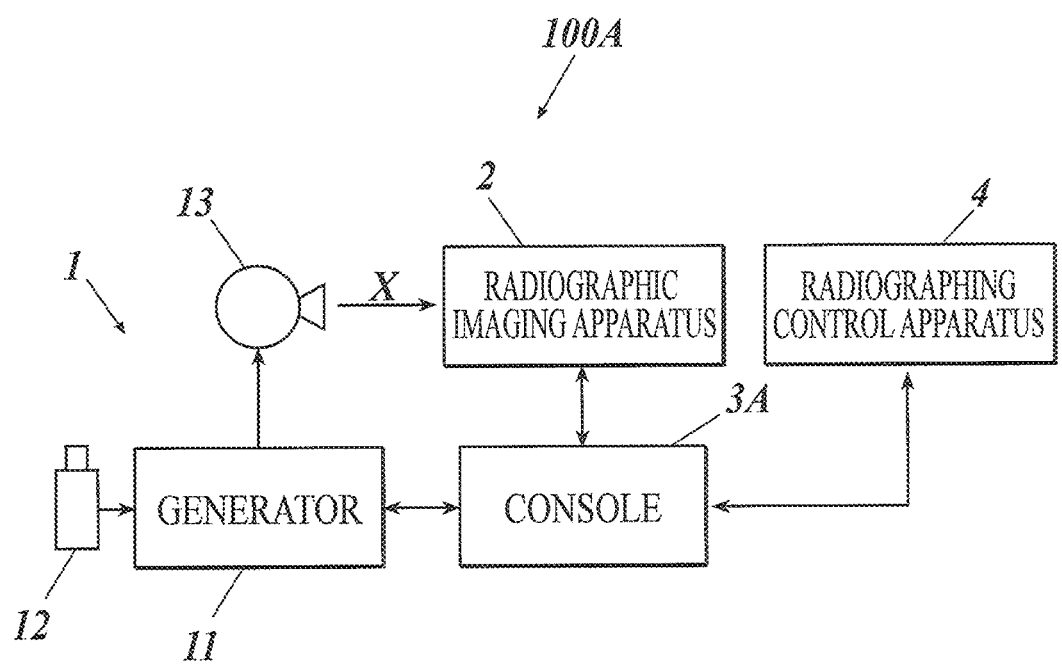
FIG. 10 is a block diagram of the configuration of the radiographic imaging system according to the second embodiment of the present invention.

A second embodiment of the present invention will be described with FIG. 10 and FIG. 3. The same reference signs are denoted to the same components as those in the first embodiment, and the description thereof is omitted.

In the radiographic imaging system 100 of the first embodiment, the console 3 serves as the radiographing control apparatus of the present invention. In a radiographic imaging system 100A of this embodiment, a console 3A does not have a function of performing the above-described radiographing control processing. Instead, the radiographic imaging system 100A includes a radiographing control apparatus 4 having a function of performing the radiographing control processing as illustrated in FIG. 10.

The radiographing control apparatus 4 is connected to an irradiating apparatus 1 and a radiographic imaging apparatus 2 via the console 3A in a wired or wireless manner so that communication is possible.

As illustrated in FIG. 3, the radiographing control apparatus 4 includes a hardware processor 41, a communicator 42, a storage 43, a display 44, an operation interface 45 and a bus 46 that connect the components with each other.

In the storage 43, a program for performing the similar processing as the above-described radiographing control processing is stored.

The components other than the storage 43, i.e. the hardware processor 41, the communicator 42, the display 44 and the operation interface 45, are the same as those of the console 3 of the first embodiment.

The radiographing control apparatus 4 of the embodiment starts the radiographing control processing when the same predetermined starting condition as in the first embodiment is satisfied.

The embodiment is an example in which the radiographing control apparatus 4 is connected to the console 3A. Instead, the radiographing control apparatus 4 may be directly connected to the irradiating apparatus 1 and the radiographic imaging apparatus 2 without an intervention of the console 3A.

The embodiment is an example in which the radiographing control apparatus 4 includes the display 44 and the operation interface 45. Instead, the radiographing control apparatus 4 may not include the display 44 and the operation interface 45, and a display 34 and an operation interface 45 of the console 3A may be used.

As described above, the console 3 or the radiographing control apparatus 4 of the radiographic imaging system 100, 100A of the first or second embodiment includes:

the image retrieving means which is capable of retrieving image data of a subject from the external radiographic imaging apparatus 2, in which the external radiographic imaging apparatus 2 is exposed to a radiation from the external irradiating apparatus 1 through the subject to generate the image data;

the total dose calculating means which calculates the total dose required to obtain the diagnostic image data to be used for diagnosis based on the pre-exposure image data, in which (i) the external radiographic imaging apparatus generates the pre-exposure image data by performing the pre-exposure to the subject at the pre-exposure dose of less than the dose of the subsequent main exposure, and (ii) the image retrieving means retrieves the pre-exposure image data;

a dose outputting means which is capable of outputting the main exposure dose based on the total dose calculated by the total dose calculating means to the external irradiating apparatus 1 and the external radiographic imaging apparatus 2; and an image compositing means which combines the main exposure image data with the pre-exposure image data to generate the diagnostic image data, in which (i) the external radiographic imaging apparatus generates the main exposure image data by performing the main exposure at the main exposure dose, and (ii) the image retrieving means retrieves the main exposure image data.

When the radiographic imaging system 100 of the embodiments is used to take a radiographic image, it is possible to determine whether a subject is in a proper position (whether it is necessary to retake a radiographic image) by using a pre-exposure image before performing a main exposure having a high dose. This can prevent a main exposure from being performed in an improper position and thereby prevent the subject from being exposed to an unnecessary radiation.

Further, the diagnostic image data is generated by combining the main exposure image data with the pre-exposure image data. This can prevent deterioration of the image quality (S/N) of the diagnostic image even when the main exposure is performed at a decreased dose.

Third Embodiment

A third embodiment of the present invention will be described referring to FIG. 1 and FIG. 2. The same reference signs are denoted to the same components as those in the first embodiment, and the description thereof is omitted.

In the radiographic imaging system 100 of the first embodiment, the console 3 serves as the radiographing control apparatus of the present invention. In a radiographic imaging system 100B of this embodiment (see FIG. 1), a console 3A does not have the function as the radiographing control apparatus. Instead, a radiographic imaging apparatus 2A has the function.

As illustrated in FIG. 2, the radiographic imaging apparatus 2A includes a hardware processor 21, a radiation detector 22, a reader 23, a communicator 24, a storage 25A and a bus 26 that connects the components to each other.

In the storage 25A, a program for performing similar processing as the above-described radiographing control processing is stored in addition to the same programs as those stored in the radiographic imaging apparatus 2 of the first embodiment.

The radiographic imaging apparatus 2A of the embodiment starts the radiographing control processing when a predetermined starting condition is satisfied, e.g. an exposure switch 12 is pressed, an irradiating apparatus 1 exposes the radiographic imaging apparatus 2A to a radiation, the radiographic imaging apparatus 2A itself generates image data, or the like.

In the embodiment, the image retrieving means of the present invention is not necessary since the radiographic imaging apparatus 2 performs the radiographing control processing. That is, the reader 23 generates pre-exposure image data and main exposure image data, which corresponds to Step S1 and Step S8 (retrieval of image data).

Since the radiographic imaging apparatus 2A does not include a display and a sound outputting means as illustrated in FIG. 2, it sends to a console 3 a signal representing an instruction to give a warning to a user in Step S10 (radiographing termination processing).

In Step S6 (setting of main radiographing conditions), the radiographic imaging apparatus 2A output the main radiographing conditions to the irradiating apparatus 1 and sets the radiographing conditions of the hardware processor 21 to the main radiographing conditions. That is, the hardware processor 21 of the radiographic imaging apparatus 2A of the embodiment serves as a dose outputting and setting means of the present invention.

Figure 11:
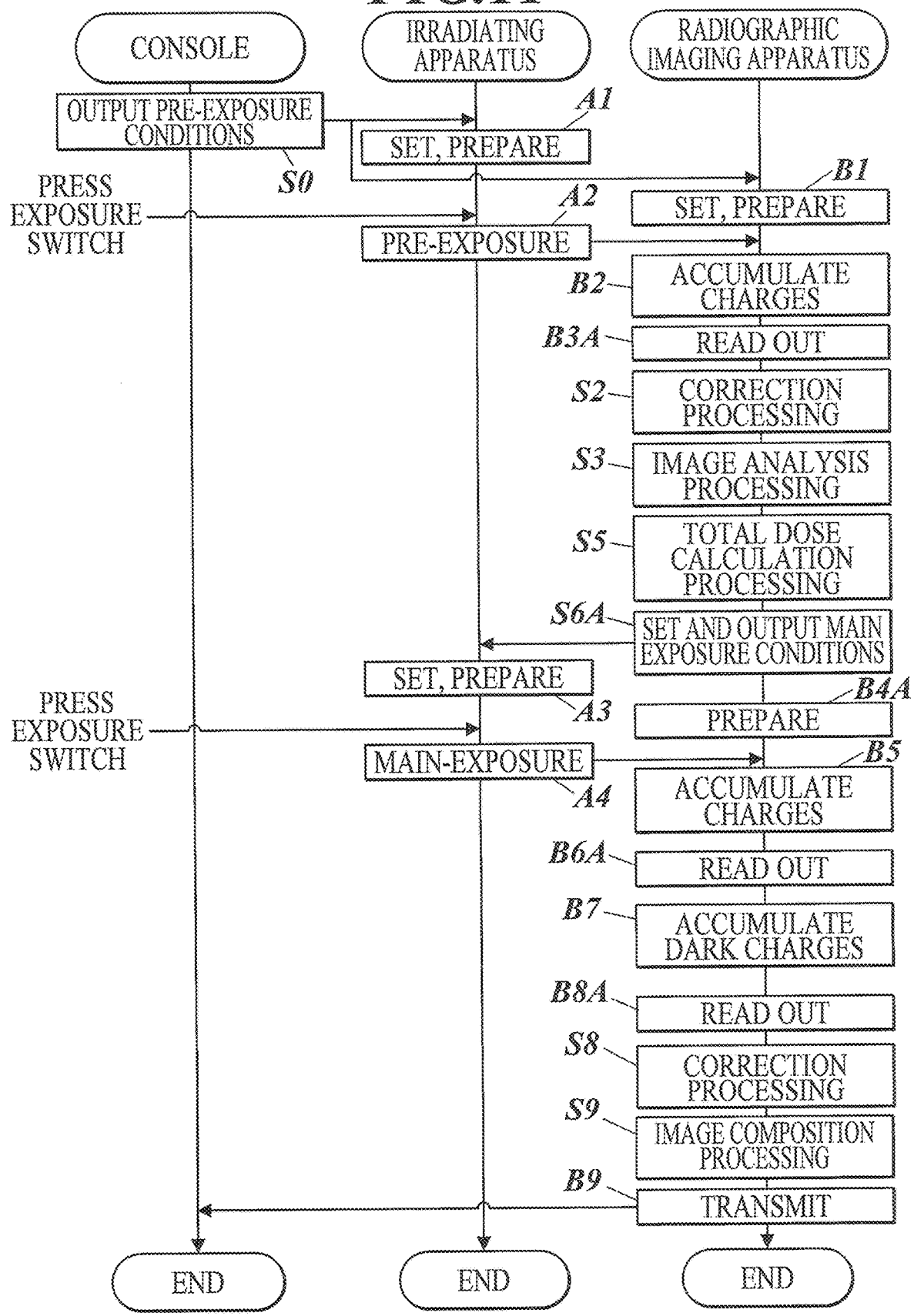
FIG. 11 is a ladder chart of an operation of the radiographic imaging system according to the third embodiment of the present invention.

A process of taking a radiographic image of a subject with the radiographic imaging system 100B of the embodiment will be described. As illustrated in FIG. 11, Step S0 to Step B2 are performed in the same manner as in a process of taking a radiographic image with the radiographic imaging system 100 of the first embodiment.

Then, the radiographic imaging apparatus 2A converts charges of the pixels to signal values and reads them as pre-exposure image data (Step B3A). In this step, the pre-exposure image data is not sent to the console 3A.

Thereafter, the radiographic imaging apparatus 2 performs Step S2 to Step S5 in the same manner as in the radiographing control processing of the first embodiment so as to set its own radiographing conditions to the main radiographing conditions and to output the main radiographing conditions to the irradiating apparatus 1 (Step S6A).

The subsequent operation of the radiographic imaging apparatus 1 is the same as that of the first embodiment.

Thereafter, the radiographic imaging apparatus 2A converts charges of the pixels into signal values and reads them as main exposure image data (Step B6A). In this step, the main exposure image data is not sent to the console 3.

Immediately before or after Step B5 and Step B6A (immediately after Step B5 and Step B6A in the example in FIG. 11), the radiographic imaging apparatus 2 converts dark charges of the pixels into signal values and reads them as offset data (Step B8A). In this step, the offset data is not sent to the console 3.

Thereafter, the radiographic imaging apparatus 2A performs Step S8 and Step S9 in the same manner as in the radiographing control processing of the first embodiment and sends generated diagnostic image data to the console 3 (Step B9).

As described above, the radiographic imaging apparatus 2A of the radiographic imaging system 100B of the third embodiment includes:

an image generating means which is exposed to a radiation from the external irradiating apparatus 1 through a subject to be able to generate image data of the subject;

a total dose calculating means which calculates a total dose required to obtain diagnostic image data to be used for diagnosis based on pre-exposure image data, in which the image generating means generates the pre-exposure image data by performing a pre-exposure to the subject at a pre-exposure dose of less than the dose of a subsequent main exposure;

a dose outputting and setting means which outputs a main exposure dose based on the total dose calculated by the total dose calculating means to the external irradiating apparatus and which sets the exposure dose of the image generating means to the main exposure dose; and an image compositing means which combines main exposure image data with the pre-exposure image data to generate the diagnostic image data, in which the image generating means generates the main exposure image data by performing a main exposure at the main exposure dose.

Even when the radiographic imaging system 100B of the embodiment is used to take a radiographic image, it is possible to prevent a main exposure from being performed in an improper position as in the first embodiment.

Further, as in the first embodiment, it is possible to prevent deterioration of the image quality (S/N) of the diagnostic image even when the main exposure is performed at a decreased dose.

Fourth Embodiment

A fourth embodiment of the present invention will be described referring to FIG. 1, FIG. 3, FIG. 12 and FIG. 13. The same reference signs are denoted to the same components as those in the first embodiment, and the description thereof is omitted.

A radiographic imaging system 100C (see FIG. 1) of the embodiment is different from the radiographic imaging system 100 of the first embodiment in the process of radiographing control processing that is performed by a console 3B or the console 3.

That is, a program stored in a storage 33A (see FIG. 3) of the console 3B is different from that of the first embodiment.

Further, in the storage 33A, various types of anatomical codes C (described in detail later) to be used in the radiographing control processing are stored.

As with the console 3 of the first embodiment, a hardware processor 31 of the console 3B of the embodiment starts the radiographing control processing when a predetermined starting condition is satisfied.

As illustrated in FIG. 12, Step S1 to Step S4 and Step S10, which is performed when the determination in Step S4 is no, of the radiographing control processing of this embodiment are the same as those of the first embodiment.

In the radiographing control processing of the embodiment, if it is determined in Step S4 that there is no abnormality, i.e. a pre-exposure is properly performed (Step S4, Yes), the hardware processor 31 performs body thickness information estimation processing (Step S5A). In this step, the hardware processor 31 estimates body thickness information of a subject based on pre-exposure image data and supplementary information associated with the pre-exposure image data.

The body thickness information to be estimated may represent a body shape such as "thin", "normal" or "thick" or a numerical value of the body thickness.

To estimate the body thickness information of a subject, techniques disclosed in JP 2016-0202219A, JP 2011-104103A and the like can be used.

Specifically, such techniques include;

a technique of voting the signal values of pixels in a region of interest in a radiographic image to a histogram and estimating body thickness information based on feature amounts calculated from the histogram;

a technique of estimating body thickness information based on the relative relationship between the width and the body thickness of a subject in a radiographic image; and estimating body thickness information based on the signal values in a subject area and the signal values in a non-subject area in a radiographic image.

The hardware processor 31 that performs this processing serves as a body thickness information estimating means of the present invention.

After estimating the body thickness information, the hardware processor 31 outputs an anatomical code C (Step S6A). In this step, the hardware processor 31 selects an anatomical code C from various types of anatomical codes C stored in the storage 33A based on the body thickness information estimated in Step S2 and outputs the selected anatomical code C to the irradiating apparatus 1 and the radiographic imaging apparatus 2.

For example, the anatomical codes C of the embodiment includes the tube voltage, the tube current, the irradiation time of the main exposure and the like as illustrated in FIG. 13.

Each anatomical code C represents a combination of a part to be radiographed and body thickness information, and the hardware processor 31 selects an anatomical code C that corresponds to the preset part to be radiographed and the body thickness information estimated in Step S2.

The hardware processor 31 that performs this processing serves as a code outputting means of the present invention.

After the hardware processor 31 outputs the anatomical code C before it performs the next Step S7, the irradiating apparatus 1 performs a main exposure to the subject in radiographing conditions based on the anatomical code C, and the radiographic imaging apparatus 2 generates main exposure image data.

Step S7 and the subsequent steps, which are performed after the radiographic imaging apparatus 2 generates the main exposure image data, are the same as those of the first embodiment as illustrated in FIG. 12.

As described above, the console 3B of the radiographic imaging system 100C of the fourth embodiment includes:

an image retrieving means which is capable of retrieving image data from the external radiographic imaging apparatus 2, in which the external radiographic imaging apparatus 2 is exposed to a radiation from the external irradiating apparatus 1 through a subject to generate the image data;

the body thickness information estimating means which estimates the body thickness information of the subject based on the pre-exposure image data, in which (i) the external radiographic imaging apparatus generates the pre-exposure image data by performing a pre-exposure to the subject at a pre-exposure dose of less than the dose of a subsequent main exposure, and (ii) the image retrieving means retrieves the pre-exposure image data;

a code outputting means which outputs to the external irradiating apparatus 1 and the external radiographic imaging apparatus 2 an anatomical code C that corresponds to the body thickness information estimated by the body thickness information estimating means; and an image compositing means which combines main exposure image data with the pre-exposure image data to generate diagnostic image data, in which (i) the external radiographic imaging means generates the main exposure image data by performing the main exposure in the radiographing conditions based on the anatomical code C, and (ii) the image retrieving means retrieves the main exposure image data.

When the radiographic imaging system 100C of the embodiment is used to take a radiographic image, it is possible to prevent the main exposure from being performed in an improper position as in the first embodiment.

Further, as in the first embodiment, it is possible to prevent deterioration of the image quality (S/N) of the diagnostic image even when the main exposure is performed at a decreased dose.

In the radiographic imaging system 100C of the embodiment, the above-described radiographing control processing is performed by the console 3B. Instead, the processing may be performed by an independent radiographing control apparatus separated from the console or by the radiographic imaging apparatus.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent applications No. 2018-006819 and No. 2018-194764, respectively filed on Jan. 19, 2018 and Oct. 16, 2018, are incorporated herein by reference in their entirety.

What is claimed is:

1. A radiographing control apparatus, comprising a hardware processor which retrieves image data of a subject from an external radiographic imaging apparatus, in which the radiographic imaging apparatus is exposed to a radiation from an external irradiating apparatus through the subject to generate the image data, retrieves pre-exposure image data which the external radiographic imaging apparatus generates by performing a pre-exposure to the subject at a pre-exposure dose of less than a dose of a subsequent main exposure, retrieves main exposure image data which the external radiographic imaging apparatus generates by performing the main exposure to the subject at a main exposure dose, and controls combining of the main exposure image data with the pre-exposure image data.

2. The radiographing control apparatus according to claim 1, wherein the hardware processor combines the pre-exposure image data with the main exposure image data by adding signal values of pixels of the pre-exposure image data respectively to signal values of pixels of the main exposure image data.

3. The radiographing control apparatus according to claim 2, wherein the hardware processor relatively decreases the signal values of the pre-exposure image data in an edge area and adds the decreased signal values.

4. The radiographing control apparatus according to claim 2, wherein the hardware processor
measures movement of the subject between the pre-exposure and the main exposure on a segment basis based on the pre-exposure image data and the main exposure image data, and
relatively enhances the signal values of the pre-exposure image data in a part where the movement is small and adds the enhanced signal values.

5. The radiographing control apparatus according to claim 2, wherein the hardware processor
measures movement of the subject between the pre-exposure and the main exposure on a segment basis based on the pre-exposure image data and the main exposure image data, and
not adds the signal values of the pre-exposure image data in a segment where the movement is larger than a predetermined value.

6. A radiographic imaging apparatus, comprising a hardware processor which is exposed to a radiation from an external irradiating apparatus through a subject to generate image data of the subject, generates pre-exposure image data which is generated by performing a pre-exposure to the subject at a pre-exposure dose of less than a dose of a subsequent main exposure, and generates main exposure image data by performing the main exposure to the subject at the main exposure dose, and controls combining of the main exposure image data with the pre-exposure image data.

7. A radiographic imaging system, comprising:
an irradiating apparatus which emits a radiation;
a radiographic imaging apparatus which is exposed to the radiation to generate image data of a radiographic image; and
the radiographing control apparatus according to claim 1.

8. A radiographic imaging system, comprising:
an irradiating apparatus which emits a radiation; and
the radiographic imaging apparatus according to claim 6.

9. A non-transitory computer readable storage medium storing a program that causes a computer to
retrieve image data of a subject from an external radiographic imaging apparatus, in which the radiographic imaging apparatus is exposed to a radiation from an external irradiating apparatus through the subject to generate the image data,
retrieve pre-exposure image data which the external radiographic imaging apparatus generates by performing a pre-exposure to the subject at a pre-exposure dose of less than a dose of a subsequent main exposure,
retrieve main exposure image data which the external radiographic imaging apparatus generates by performing the main exposure to the subject at a main exposure dose, and
control combining of the main exposure image data with the pre-exposure image data.

* * * * *